US00PP26497P2

(12) United States Plant Patent
Bernabe

(10) Patent No.: US PP26,497 P2
(45) Date of Patent: Mar. 8, 2016

(54) ***SALVIA* PLANT NAMED 'BLUE NOTE'**

(50) Latin Name: ***Salvia* hybrid**
Varietal Denomination: Blue Note

(71) Applicant: Catherine Bernabe, El Campello (ES)

(72) Inventor: Catherine Bernabe, El Campello (ES)

( * ) Notice: Subject to any disclaimer, the term of this patent is extended or adjusted under 35 U.S.C. 154(b) by 161 days.

(21) Appl. No.: 13/998,091

(22) Filed: Sep. 30, 2013

(51) Int. Cl.
*A01H 5/02* (2006.01)

(52) U.S. Cl.
USPC ..... Plt./475

(58) Field of Classification Search
USPC ..... Plt./475
See application file for complete search history.

(56) References Cited

PUBLICATIONS

Appleby. Nurseries buoyed by sales pick-up ahead of National Plant Show Jun. 21, 2013 retrieved on May 14, 2015, retrieved from the Internet at <http://www.hortweek.com/nurseries-buoyed-sales-pick-up-ahead-national-plant-show/article/1186669> pp. 1-9.*
McHutchison Florexpo Unrooted Cuttings 2012-2013 retrieved on May 14, 2015, retrieved from the Internet at <http://mchutchison.com/McH_Florexpo_12-13.pdf> pp. 1-3, 29 and 98-100.*
New Plants and Flower Jun. 1, 2012 retrieved on May 19, 2015, retrieved from the Internet at <http://www.newplantsandflowers.com/french-salvia-hybrids-on-dutch-trade-fair/> 2 pp.*

* cited by examiner

*Primary Examiner* — June Hwu
(74) *Attorney, Agent, or Firm* — Penny J. Aguirre

(57) ABSTRACT

A new cultivar of hybrid *Salvia*, 'Blue Note' that is characterized by its compact plant habit, its fragrant deep blue-purple flower on purple tinged flowering stems, and its long flowering period.

2 Drawing Sheets

Botanical classification: *Salvia* hybrid.
Variety denomination: 'Blue Note'.

BACKGROUND OF THE INVENTION

The present invention relates to a new and distinct cultivar of *Salvia* of hybrid origin and will be referred to hereafter by its cultivar name, 'Blue Note'. 'Blue Note' is an herbaceous perennial grown for landscape use.

The new *Salvia* resulted from a controlled breeding program conducted by the Inventor in Henansal, France. The Inventor made crosses in 2008 between unnamed proprietary plants of interspecific hybrid origin (*Salvia chamaedryoides*× *Salvia lycoides*) in the Inventor's breeding program as both the female and male parents. The characteristics of the parents are unknown as seeds where pooled and sown from several crosses. 'Blue Note' was selected as a single unique plant in 2008 from the resulting seedlings of the above crosses.

Asexual propagation of the new cultivar was first accomplished by the Inventor by vegetative stem cuttings in 2009 in Henansal, France. Asexual propagation by vegetative stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Blue Note' as a unique cultivar of *Salvia*.

1. 'Blue Note' exhibits a compact plant habit.
2. 'Blue Note' exhibits fragrant deep blue-purple flower on purple tinged flowering stems.
3. 'Blue Note' exhibits a long flowering period; blooming from spring to first frost in France.

'Blue Note' can be most closely compared to plants of the species *Salvia chamaedryoïdes* and *Salvia lycioïdes*. Plants of *Salvia chamaedryoïdes* differ from 'Blue Note' in having a less vigorous growth habit and in having fewer flowers that are lighter in color. Plants of *Salvia lycioïdes* differ from 'Blue Note' in having leaves that are less round in shape and in having flowers that are less blue in color.

BRIEF DESCRIPTION OF THE DRAWING

The accompanying colored photographs illustrate the overall appearance and distinct characteristics of a one year-old plant of the new *Salvia* as grown in a greenhouse in a 15-cm container in Henansal, France.

The photograph in FIG. 1 provides a side view of 'Blue Note' in bloom.

Figure 1:
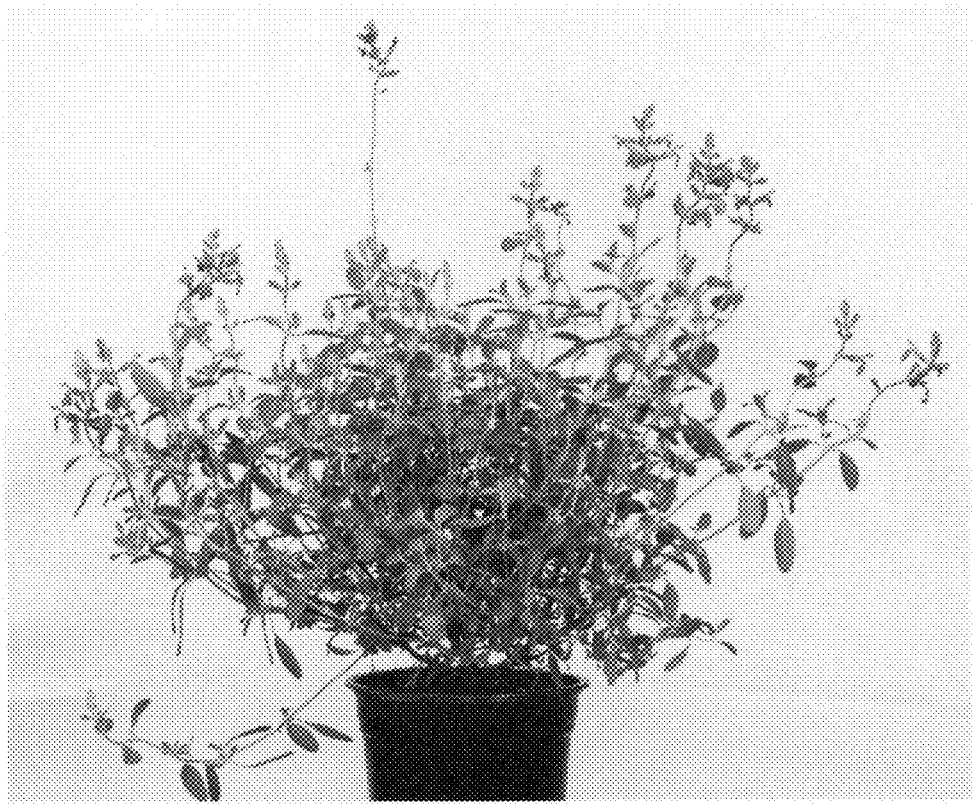
Figure 2:
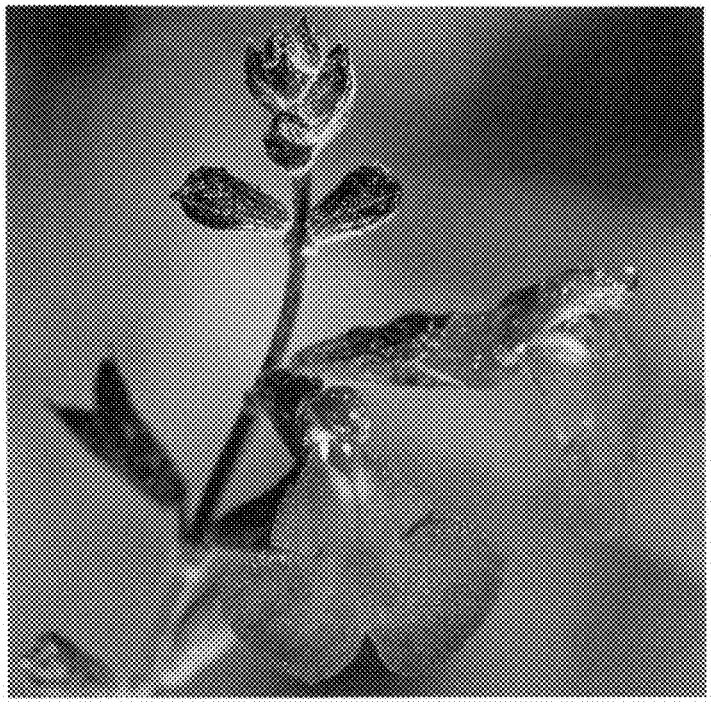

The photograph in FIG. 2 provides a close-up view of flowers of 'Blue Note'.

Figure 3:
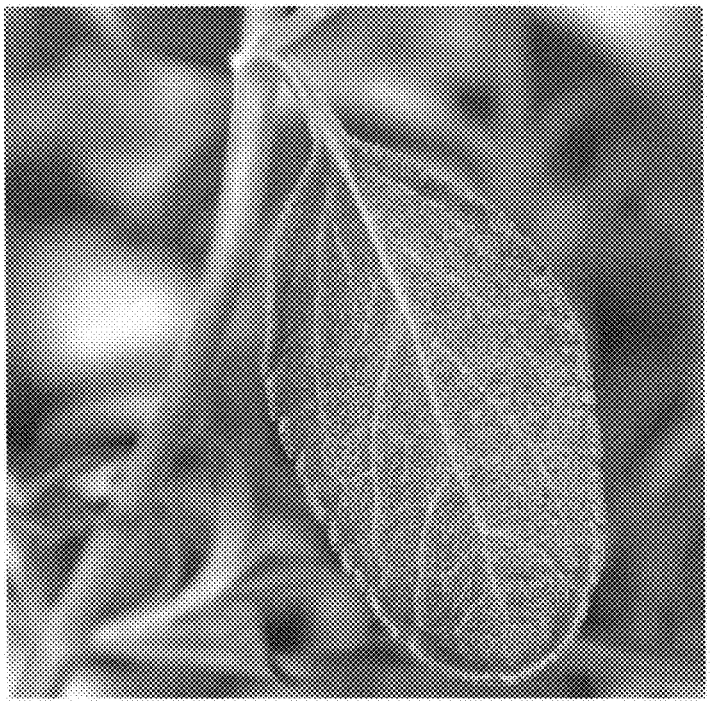

The photograph in FIG. 3 provides a close-up view of the foliage of 'Blue Note'. The colors in the photographs may differ slightly from the color values cited in the detailed botanical description, which accurately describe the colors of the new *Salvia*.

DETAILED BOTANICAL DESCRIPTION

The following is a detailed description of one year-old plants of 'Blue Note' as grown in a greenhouse in 15-cm containers in Henansal, France. Plants were grown under average day temperatures ranging from +14° to +30° C. and average night temperatures of +8° to +18° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—From May to first frost in Henansal, France.

*Plant type*.—Herbaceous perennial.

*Plant habit*.—Broad upright, compact.

*Plant size*.—Reaches up to 50 cm in height and spread.

*Cold Hardiness*.—At least in U.S.D.A. Zone 8.

*Diseases and pests*.—No susceptibility or resistance to diseases or pests have been observed.

*Root description*.—Fibrous, non-spreading.

*Propagation*.—Vegetative stem cuttings.

*Growth rate*.—Moderate.

Stem description:

*Shape*.—Rounded.

*Stem color*.—144A.

*Stem size*.—Average of 16.2 cm in length and 1.5 mm in diameter.

*Stem surface*.—Slightly glossy and moderately to densely covered with very short soft hairs; average 0.2 mm in length and 157D in color.

*Stem fragrance*.—When rubbed the leaves give a "sage" like fragrance.

*Internode length*.—Average of 4 cm.

*Branching*.—Average of 9 main stems, an average of 10 lateral braches per main stem.

Foliage description:

*Leaf shape*.—Ovate to elliptic.

*Leaf division*.—Simple.

*Leaf base*.—Short attenuate.

*Leaf apex*.—Obtuse.

*Leaf fragrance*.—When rubbed the leaves give a "sage" like fragrance.

*Leaf venation*.—Pinnate, upper and lower surface 146C in color.

*Leaf margins*.—Undeeply crenate.

*Leaf arrangement*.—Opposite.

*Leaf attachment*.—Petiolate.

*Leaf surface*.—Very slightly rugose on both surfaces, upper surface slightly glossy and slightly pubescent, lower surface dull.

*Leaf size*.—Up to 3.1 cm in length and 1.3 cm in width.

*Leaf color*.—Young leaves; upper surface 137B, lower surface 137D, mature leaves; upper surface a color between 137A and N137D, lower surface a color between 138A and N138B.

*Leaf quantity*.—Average of 10 (5 pairs).

*Petioles*.—Up to 1.3 cm in length and 1 mm in diameter, 144B in color, slightly pubescent surface.

Inflorescence description:

*Inflorescence type*.—Terminal verticillaster, individual flowers are in whorls.

*Lastingness of inflorescence*.—Approximately 5 days.

*Inflorescence size*.—An average of 9.2 cm in length and 3.8 cm in width.

*Flower type*.—Labiate.

*Flower number*.—An average of 40 per vertillicaster, flowers in whorls, average of 4 flowers per whorl.

*Flower fragrance*.—Sage scented.

*Flower buds*.—Obovate in shape, average of 0.8 cm in length and 3 mm in diameter, 138B in color with upper side near apex tinged with N186A to N186B, immature petals portion near apex 93A.

*Flower size*.—About 2.1 cm in depth and about 1.4 cm in width (horizontal) and 1.8 cm in height (vertical).

*Peduncle*.—An average of 15.9 cm in length and 1.5 mm in width, held straight on top of lateral branch, strong in strength, color; 144B to 144C with sunny side tinged N186A.

*Pedicels*.—About 2 mm in length and 1 mm in diameter, color; 146B and tinged N186A.

*Calyx*.—Campanulate in shape, average of 0.9 cm in length and 2 mm in width (horizontal), and 5 mm in height (vertical).

*Sepals*.—3, campanulate in arrangement, narrow obovate in shape with lower 70% fused, entire margin, acute apex, cuneate base fused into tube, surface is dull and covered with very short glandular hairs, average of 0.4 mm in length and 186C to 186D in color, average of 0.9 cm in length and 2 mm in width, color: immature upper (inner) side; 138B, slightly striped with 146B, immature lower (outer) side; upper side 146A to 146B, tinged and striped N186A, lower side 144C, mature upper (inner) side; 146B, striped with 147A, mature lower (outer) side; 146A to 146B, tinged and striped N186A, under side 144C.

*Petals*.—2, labiate, arranged in 2 lips fused 55% into tube at base, upper lip; broad elliptic and folded in shape, entire margin, retuse apex, 2 cm in length and 3 mm in width, lower lip; broad spathulate in shape, two-lobed margin, retuse apex, 2.4 cm in width and 1.4 cm in length, tube; 1 cm in length and 3 mm in width, color: when opening upper (inner) side; upper and lower lip N89B to N89C, inside of tube 90B to 90C, when opening lower (outer) side; N89C, tube 90B, base of lower lip 92B, when fully open upper (inner) side; upper and lower lip a color between N89D and 90A, inside of tube 90C, when fully open lower (outer) side; upper and lower lip N89D, tube 90B, base of lower lip 92B, color fading on all to 93A.

Reproductive organs:

*Gynoecium*.—1 pistil, about 1.8 cm in length, style is 1.5 cm in length and NN155D in color, stigma is cleft (2 parted) and 90B in color, ovary is 145D in color.

*Androcoecium*.—2 stamens, filaments are N155B with base 91C to 91D in color and about 1 cm in length, anthers are dorsifixed, narrowly elliptic in shape, an average of 1.5 mm in length and 203B in color, pollen is moderate in quantity and about 13A in color.

*Fruit and seed*.—Observed to be sterile with no viable seeds formed.

It is claimed:

1. A new and distinct cultivar of *Salvia* plant named 'Blue Note' as herein illustrated and described.

* * * * *